United States Patent [19]
Chafetz et al.

[11] 4,248,719
[45] Feb. 3, 1981

[54] QUATERNARY AMMONIUM SALTS AND LUBRICATING OIL CONTAINING SAID SALTS AS DISPERSANTS

[75] Inventors: Harry Chafetz, Poughkeepsie, N.Y.; Gary D. Lee, Spring, Tex.

[73] Assignee: Texaco Inc., White Plains, N.Y.

[21] Appl. No.: 69,450

[22] Filed: Aug. 24, 1979

[51] Int. Cl.³ .................. C07D 207/12; C10M 1/20; C10M 1/32
[52] U.S. Cl. ........................... 252/34; 252/51.5 A; 260/326.44
[58] Field of Search ............... 252/34, 51.5 A; 260/326.44

[56] References Cited

U.S. PATENT DOCUMENTS

| | | | |
|---|---|---|---|
| 3,172,892 | 3/1965 | LeSuer et al. | 252/51.5 A |
| 3,272,746 | 9/1966 | LeSuer et al. | 252/51.5 A |
| 3,630,902 | 12/1971 | Coupland et al. | 252/51.5 A |

FOREIGN PATENT DOCUMENTS 741566  12/1970  Belgium ........................ 252/51.5 A Primary Examiner—W. J. Shine
Attorney, Agent, or Firm—Carl G. Ries; Robert A. Kulason; Henry W. Archer

[57] ABSTRACT

Quaternary ammonium salts prepared by reacting an alkenylsuccinimide with a monocarboxylic acid ester provide improved dispersancy in lubricating oils, as compared with the starting alkenylsuccinimides.

8 Claims, No Drawings

QUATERNARY AMMONIUM SALTS AND LUBRICATING OIL CONTAINING SAID SALTS AS DISPERSANTS

BACKGROUND OF THE INVENTION

1. Field of the Invention

This invention relates to a novel class of detergent dispersant compounds which inhibit or prevent the formation of sludge or varnish in lubricants intended for use in the crankcase of internal combustion engines, gears and other power transmitting units. More specifically, the invention concerns compounds of the above described type which are prepared by a process offering the economic advantage of avoiding the formation of contaminating inorganic by-products and eliminates the need for special equipment in handling volatile and dangerous materials. The process further has the improved feature of employing a simplified purifying step.

2. Description of the Prior Art

The prior art to which this invention relates are U.S. Pat. Nos. 3,172,892 and 3,272,746, which describe the thermal reaction products of alkenylsuccinic anhydride with amines; and Japanese Pat. No. 7,342,603, which describes the preparation of quaternary ammonium salts from amines and carboxylic acid esters. The latter patent indicates that pyridine and methyl salicylate can be refluxed to yield 1-methylpyridinium salicylate and that the salicylates of $Et_3N^+Me$, $PhCH_2N^+Et_3$, $HOCH_2CH_2N^+MeEt_2$; methyl-ethyl-and propylisoquinolinium cations can be similarly prepared. Also relevant is coassigned U.S. Pat. No. 4,048,080 which describes and claims amine alkenylsuccinic acid or anhydride reaction products which can be used as one of the starting products here. This patent accordingly is incorporated by reference in the present disclosure.

OBJECTS AND SUMMARY OF THE INVENTION

It is a principal object of this invention to provide compositions which are effective as dispersants-detergents in lubricating fluids.

It is another object of the invention to provide improved hydrocarbon oil compositions. These and other objects are achieved in accordance with the invention by providing quaternary ammonium salts of carboxylic acid esters wherein the carboxyl portion of the ester is stabilized.

A critical aspect of this invention is that the carboxyl portion of the ester must be stabilized in order to participate in the quaternization reaction. Thus substituted aryl derived carboxylic acids are preferred, particularly those having ortho hydroxyl groups. The preparation of the salts of the invention can be illustrated by the following general equation:

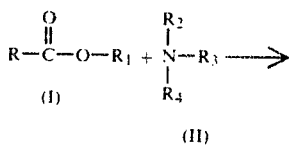

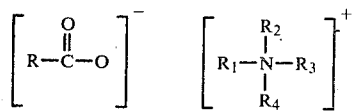

wherein R is nitro, cyano, carboalkoxy, or hydroxy substituted aryl group having 6 to 10 carbon atoms where the aryl group is derived from benzene or naphthalene (phenyl or naphthyl); $R_1$ is a lower alkyl ($C_1-C_5$) group; $R_2$ and $R_3$ are the same or different alkyl groups having from 1 to 8 carbon atoms; and $R_4$ is an alkenylsuccinimidyl alkyl or alkenylsuccinoxyalkyl group having from 60 to 200 aliphatic carbon atoms. For a typical salt, R can be 2-hydroxybenzene; $R_1$, $R_2$ and $R_3$ methyl; and $R_4$ polybutenylsuccinimidyl ethyl having about 100 carbon atoms.

The formation of quaternary ammonium salts (III) is indicated by infrared and n.m.r. spectroscopy. Preferably, the starting succinimides or succinate esters are prepared by reacting an alkenylsuccinic anhydride, having the structural unit represented by the formula:

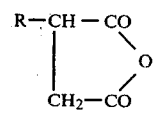

wherein R is an alkenyl radical having an average molecular weight ranging from about 800 to 3,000, with an amine, represented by the formula:

wherein R' and R" represent alkyl radicals having from 1 to 8 carbon atoms, X is a divalent hydrocarbon radical having from 2 to 8 carbon atoms and Y is a radical, selected from the group consisting of amino, hydroxy and a radical having the formula $O(R'''O)_xH$ in which R''' is an alkylene radical having from 2 to 3 carbon atoms an X is an integer from 1 to 5; using a molar proportion of said amine to said alkenylsuccinic anhydride greater than 1.

The alkenyl radical on the above-described alkenylsuccinic anhydride reactant has an average molecular weight ranging from about 800 to 3,000, as determined by the ASTM Method D-2503. A preferred alkenylsuccinic anhydride starting reactant is one in which the alkenyl radical has an average molecular weight ranging from about 1,000 to 2,000, with the particularly preferred species having a molecular weight ranging from about 1,250 to 1,500.

In practice, the reaction of this invention is carried out by heating an ester (I) with an alkenylsuccinimide or ester (II), in a ratio of 0.5 to 3.0 moles to 1, to a temperature in the range of 100° to 180° C. for a reaction time dependent upon the temperature utilized during the reaction. The reaction can be carried with or without a solvent inert to the reactants.

The selection of appropriate solvent depends upon the desired reaction temperature and mutual solubility of the reactants. No solvent is required if the reactants form a homogeneous solution at the reaction temperature. Purification of the recovered product can be effected with a neutral solvent such as hexane. Excess carboxylic acid ester, if used in the reaction, can be removed by stripping at reduced pressure or by methanol extraction. The starting alkenylsuccinimides preferably are prepared as shown below from alkenylsuccinic anhydrides which are themselves prepared by heating maleic anhydride with a high molecular weight olefin or a chlorinated hydrocarbon.

The invention is further illustrated in non-limiting fashion by the following examples:

EXAMPLE 1

Preparation of the starting alkenylsuccinimides from alkenylsuccinic acid anhydride (ASAA) and N,N-dimethyl-aminopropylamine (DMAPA).

DMAPA (27.0 g., 0.27 mole) was charged to a 1-liter 4-neck flask fitted with a stirrer, thermocouple, thermometer, nitrogen inlet tube, Dean-Stark water separator with condenser, and an addition funnel. ASAA (558 g., 0.30 mole active) was charged through the addition funnel with stirring.

The ASAA was prepared by a thermal reaction of polyisobutylene (PIB), with an average molecular weight of about 1300, and maleic anhydride (MA). After the addition was complete (about one hour), a reaction temperature of 160° C. was obtained and maintained for three hours. About 1.2 ml. overhead was collected in the water trap. The sample was filtered hot through filter aid.

Yield=499 g.

Analysis: % N 1.1, TBN 23.4

EXAMPLE 2

One hundred gram of the product obtained in Example 1 was dissolved in 300 ml. of hexane and extracted with 2×200 ml. of methanol. The solvents were removed at 100° C./25 mm Hg.

Yield=83 g.

Analysis: % N 0.70, TBN 16.3

EXAMPLE 3

The product obtained in Example 1 (100 g.) and 8.2 g. of methyl salicylate (MS) were charged in approximately a 1 to 1 mole ratio to a 250 ml. 3-neck flask fitted with a gas inlet tube, stirrer, thermometer, thermocouple, and reflux condenser and heated with stirring at 160° C. for 16 hours. The sample was dissolved in 300 ml. hexane and methanol extracted (2×200 ml.). After filtering through a filter aid, the solvents were removed at 100° C./25 mm. Hg.

Yield=80 g.

Analysis: % N 0.51, TBN 11.2

EXAMPLE 4

Following the procedure of Example 3 except that a mole ratio of Example I product to MS of 1 to 2 was used in the reaction, there was obtained a yield of 70 grams of a product which analyzed: % N, 0.41, TBN 11.5.

EXAMPLE 5

ASAA (1000 g., 0.48 mole active) and 100 gm. DMAPA (1.44 mole were charged to a 3-liter 3-neck flask fitted with a nitrogen inlet, stirrer, thermocouple, thermometer, and a Dean-Stark water separator with condenser. The ASAA used in this preparation contained about 6% diluent oil. The contents were heated at 100° C., for two hours then for one hour at 160° C. The sample was dissolved in 1500 ml. heptane and methanol extracted, 2×1000 ml. The solvents were removed at 100° C./25 mm. Hg.

Yield=953 g.

Analysis: % N 1.04, TBN 20.1

EXAMPLE 6

The product from Example 5 (100 gm.) and 35 gm. MS (approximately a mole ratio of 1 to 5) were treated as in Example 3 except, in this instance, a reaction temperature of 150° C. for 24 hours was utilized. There was obtained 82 gm of a product which gave the analysis: % N 0.61, TBN 12.8

The salts above disclosed find their principal utility as dispersants-detergents.

The lubricant compositions of the invention comprise a major amount of hydrocarbon oil of lubricating viscosity and a detergent-dispersant amount of the aforedescribed salts. Advantageously, in the finished lubricating oil compositions, the reaction product content ranges between about 0.1 and 10 wt. %, preferably between about 0.5 and 5 wt. %.

Examples of the hydrocarbon base oils contemplated herein are the naphthenic base, paraffinic base and mixed base mineral oils, and other oils such as synthetic oils, e.g., alkylene polymers such as polypropylene and polyisobutylene of a molecular weight of between about 250 and 2500. Advantageously, a lubricating base oil having a lubricating oil viscosity at 100° F. of between 50 and 2,000, preferably between about 100 and 600, is normally employed for the lubricant compositions and concentrates thereof (SUS basis).

In the contemplated finished lubricating oil compositions other additives may be included in addition to the nitrogenous dispersant of the invention. These additives may be any of the suitable standard pour depressants, viscosity index improvers, oxidation and corrosion inhibitors, anti-foamants, supplementary detergent-dispersants, etc. Exactly what additional additives are included in the finished oils and the particular amounts thereof will depend on the particular use and conditions desired for the finished oil product.

Specific examples of such supplementary additives are as follows:

A widely used and suitable VI improver is the polymethacrylate having the general formula:

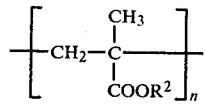

where $R^2$ is an aliphatic radical of from 1 to 20 carbons and n is an integer of between about 600 and 35,000. One of the most suitable VI improvers is the tetrapolymer of butyl methacrylate, dodecyl methacrylate, octadecyl methacrylate and dimethylaminoethyl methacrylate having a respective component weight ratio in the polymer of about 4:10:5:1. The improvers are normally employed in the finished lubricant compositions in quantities between about 0 and 10 wt. %.

One of the commonly employed lube oil corrosion inhibitors are the divalent dialkyl dithiophosphates resulting from the neutralization of a $P_2S_5$-alcohol reaction product with a divalent metal or divalent metal oxide. Barium, zinc, and dialkyl dithiophosphates are specific examples. Another class of antioxidants are the polyalkylated diphenylamines such as a mixture of 2,2'- diethyl-4,4'-dioctylphenylamine and 2,2'-diethyl-4-p-octyl-diphenylamine. The corrosion and oxidation inhibitors are usually present in the finished lubricating oil composition in concentrations of between about 0.1 and 3 wt. %.

Examples of supplementary detergent-dispersants which can be employed are the monoethoxylated inorganic phosphorus acid free, steam hydrolyzed polyalkylene (500–5000 mol wt)-$P_2S_5$ reaction product, alkaline earth metal alkylphenolates such as barium nonylphenolate, barium dodecylcresolate, calcium dodecylphenolate and the calcium carbonate overbased calcium alkaryl sulfonates formed by blowing a mixture of calcium hydroxide and calcium alkaryl sulfonate, e.g., calcium alkylbenzene sulfonate of about 900 m.w. with carbon dioxide to form a product having a total base number (TBN) of 50 or more, e.g., 300 to 400.

If antifoamants are employed in the finished compositions, one widely used class thereof which is suitable are the dimethyl silicone polymers employed in amounts of between about 10 and 1000 ppm.

The products of the invention were evaluated by blending in a multigrade (10W-30) oil which contained also 0.23% of a nominal 18:1 overbased calcium sulfonate detergent-dispersant; 0.15% zinc alkyldithiophosphate anti-oxidant; 0.25% of a mixture of ethyl substituted mono-and dinonyldiphenylamines serving as anti-oxidants; 0.1% of a polymethacrylic VI improver; 0.15% of a dimethyl silicone anti-foaming agent; and 11–13% of an oil solution of an ethylene-propylene copolymer of 20,000 to 50,000 molecular weight.

The additives of the invention were tested for effectiveness in the above oil blend by the Bench V-C test. This test is conducted by heating the test oil mixed with a synthetic hydrocarbon blowby and a diluent oil at a fixed temperature for a fixed period of time. After heating, the turbidity of the resultant mixture is measured. A low percentage (0-10) is indicative of good dispersancy by the additives while high values (20-100) are indicative of oils of increasingly poorer dispersancy.

In the table below, the 3 References are FREO #126, 127 and 179 Standards for good, medium and poor dispersancy, respectively.

| Products from Example No. | % Oil | Wt. % | % Turb. | References |
|---|---|---|---|---|
| 1 | 0 | 2 | 54.0 | 2.5, 15, 70 |
|  |  | 3 | 33.0 | 2.5, 15, 70 |
| 2 | 0 | 2 | 44.0 | 2.5, 15, 70 |
|  |  | 3 | 25.0 | 2.5, 15, 70 |
| 3 | 0 | 2 | 20.0 | 2.5, 15, 70 |
|  |  | 3 | 6.0 | 2.5, 15, 70 |
| 4 | 0 | 2 | 10.0 | 2.5, 15, 70 |
|  |  | 3 | 11.5 | 2.5, 15, 70 |
| 5 | 6 | 2 | 56.0 | 1.5, 20, 53 |
|  |  | 3 | 53.0 | 2, 20, 60 |
| 6 | 6 | 2 | 37.0 | 1.5, 20, 53 |
|  |  | 3 | 15.0 | 2, 20, 60 |

VC TEST RESULTS

The foregoing test results show that the oil compositions of the invention (3,4 and 6) meet the requirements of the dispersancy test, and are superior in each case to the results obtained with the reference succinimides used in Examples 1, 2 and 5 by being less turbid.

Advantageously in this invention, no halide derivatives are obtained which is in contrast to the formation of quaternary ammonium salts using alkyl halides and amines. As a result, products are more easily purified and concern over the corrosiveness of halide contamination is negated. Also, this invention avoids special equipment needed for handling volatile and dangerous materials such as methyl halides and dimethyl sulfoxide. The dispersancy of the quaternized materials is significantly improved over the starting alkenylsuccinimides, as shown in the above table.

The present invention may be embodied in other specific forms without departing from the spirit or essential attributes thereof and accordingly, reference should be made to the appended claims, rather than to the foregoing specifcation as indicating the scope of the invention.

We claim:

1. A quaternary ammonium salt suitable as a detergent-dispersant in lubricating oils, said salt having the formula:

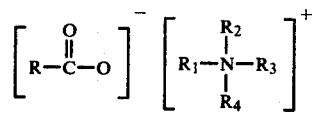

wherein R is a substituted aryl group having from 6 to 10 carbon atoms; $R_1$ is a lower alkyl group of 1 to 5 carbon atoms, $R_2$ and $R_3$ are the same or different alkyl groups having from 1 to 8 carbon atoms and $R_4$ is an alkenylsuccinimidyl alkyl or an alkenylsuccinoxy alkyl group having from 60 to 200 carbon atoms.

2. The salt of claim 1, wherein R is 2-hydroxybenzene; $R_1$, $R_2$, and $R_3$ are methyl, $R_4$ is polybutenylsuccinimidylethyl having about 100 carbon atoms.

3. The salt of claim 1, wherein R is a nitro, cyano, carboalkoxy or hydroxy substituted aryl group, said aryl group being phenyl or naphthyl.

4. A lubricating oil composition comprising a major proportion of a base oil of lubricating viscosity and a minor dispersant amount of a product as defined in claim 1.

5. The composition of claim 3 wherein said oil has an SUS viscosity at 100° F. of between 50 and 2000.

6. The composition of claim 3 wherein said oil has an SUS viscosity at 100° F. of between about 100 and 600.

7. The composition of claim 3 containing between about 0.1 and 10 weight percent of said product.

8. The composition of claim 3 containing between about 0.5 and 5 weight percent of said product.

* * * * *